United States Patent [19]

Mazid

[11] Patent Number: 5,149,425
[45] Date of Patent: Sep. 22, 1992

[54] AFFINITY SUPPORTS FOR HEMOPERFUSION

[75] Inventor: M. Abdul Mazid, Edmonton, Canada

[73] Assignee: Chembiomed, Ltd., Edmonton, Canada

[21] Appl. No.: 679,801

[22] Filed: Apr. 3, 1991

Related U.S. Application Data

[62] Division of Ser. No. 270,950, Nov. 9, 1988.

[51] Int. Cl.$^5$ .............................................. B01D 15/08
[52] U.S. Cl. .............................. 210/198.2; 210/502.1; 210/635; 210/656; 502/402; 502/404
[58] Field of Search ................ 502/402, 404; 210/635, 210/656, 198.2, 502.1, 506, 500.34, 500.41; 264/48, 49; 427/221, 222, 245, 294, 296; 604/6

[56] References Cited

U.S. PATENT DOCUMENTS

| | | | |
|---|---|---|---|
| 3,577,226 | 5/1972 | Elbert | 29/182 |
| 3,725,113 | 4/1973 | Chang | 424/36 |
| 3,795,313 | 3/1974 | Kirkland et al. | 210/198.2 |
| 3,808,125 | 4/1974 | Good | 210/656 |
| 3,878,092 | 4/1975 | Fuller | 210/656 |

(List continued on next page.)

FOREIGN PATENT DOCUMENTS

| | | | |
|---|---|---|---|
| 0105579 | 4/1984 | European Pat. Off. | 210/198.2 |
| 0129905 | 1/1985 | European Pat. Off. | 210/198.2 |
| 0172579 | 2/1986 | European Pat. Off. | 210/198.2 |
| 0165912 | 12/1987 | European Pat. Off. | 210/198.2 |
| 3617672 | 12/1987 | Fed. Rep. of Germany | 210/198.2 |
| 367063 | 2/1988 | Fed. Rep. of Germany | 210/198.2 |
| 2239282 | 2/1975 | France | 210/198.2 |
| 2436607 | 4/1980 | France | 210/198.2 |

OTHER PUBLICATIONS

Refojo, J. Ap. Poly. Sci. (1965) 9:3417ƒ3125.
White, J. Phys. Chem. (1960) 64:1563–1565.
Schenkein et al., J. Clin. Invest. (1971) 50:1864–1868.
Lyle et al., J. Immunol. (1974) 113:517–521.
Terman et al., Clin. Exp. Immunol. (1977) 28:180–188.
Terman et al., New Eng. J. Med. (1981) 305:1195–1200.
Besa et al., Amer. J. Med. (1981) 71:1035–1040.
Messaikeh et al., Biological and Biomechanical Performance of Biomaterials (1986) Christel et al., Eds., Elsevier, Amsterdam pp. 321–326.
Margel et al., Ap. Biochem. Biotechnol. (1986) 12:37–66.
Bensinger et al., Transfusion (1981) 21:335–342.
Bensinger et al., New Eng. J. Med. (1981) 304:160–162.
Bensinger et al., J. Clin. Apheresis (1982) 1:2–5.
Bensinger et al., Vox Sang (1985) 48:357–361.
Chang, Trans. Amer. Soc. Artif. Int. Organs (1980) 26:546–549.
Osterwalder et al., Blut (1986) 53:379–390.
Bussel et al., Plasma Ther. Trans. Technol. (1985) 6:461–464.
Raja et al., Trans. Amer. Soc. Artif. Internal Organs (1986) 32:102–103.

(List continued on next page.)

Primary Examiner—Ernest G. Therkorn
Attorney, Agent, or Firm—Morrison & Foerster

[57] ABSTRACT

A method of coating chromatographic particulate supports to provide a biocompatible outer layer of synthetic membrane-type film which prevents the release of fines but permits the adsorption of components to an affinity ligand is described. The matrix is provided with a membrane-type coating, which prevents leaching of fines, with a pore size of at least 20 angstroms. The coating is applied to a solid particulate under conditions where an integral membrane coat will be formed. It may also be necessary to control the size and number of pores of the membranes by treating a suspension of the solid support in a solvent which contains 0.1–1% of the support weight of a biocompatible polymer along with 0.5–5% of the weight of said polymer of a dissolved compatible pore-controlling component. The solvent is then removed from the suspension and the membrane-coated material used in extracorporeal treatment of body fluids or in other chromatographic techniques. The coating process can be conducted before or after the particulate support is functionalized and/or derivatized.

14 Claims, 6 Drawing Sheets

U.S. PATENT DOCUMENTS

| | | | |
|---|---|---|---|
| 3,953,360 | 4/1976 | Morishita et al. | 502/402 |
| 3,954,678 | 5/1976 | Maquisee | 502/402 |
| 3,983,053 | 9/1976 | Courtney et al. | 502/402 |
| 3,983,299 | 9/1976 | Regnier | 428/405 |
| 4,029,583 | 6/1977 | Ho Chang et al. | 55/67 |
| 4,051,300 | 9/1977 | Klein et al. | 210/500.28 |
| 4,070,348 | 1/1978 | Kraemer | 260/793 |
| 4,076,892 | 2/1978 | Fennimore et al. | 502/402 |
| 4,104,209 | 8/1978 | Mikes et al. | 521/62 |
| 4,137,401 | 1/1979 | Lemieux et al. | 536/116 |
| 4,140,652 | 2/1979 | Korshak et al. | 252/426 |
| 4,140,653 | 2/1979 | Imura et al. | 502/402 |
| 4,163,725 | 8/1979 | Sano et al. | 210/490 |
| 4,171,283 | 10/1979 | Nakashima | 502/402 |
| 4,177,038 | 12/1979 | Biebricher et al. | 210/656 |
| 4,238,473 | 12/1980 | Lemieux et al. | 536/116 |
| 4,248,736 | 2/1981 | Fuchigami et al. | 502/402 |
| 4,250,256 | 2/1981 | Wielinger et al. | 435/810 |
| 4,332,694 | 6/1982 | Kalal et al. | 252/189 |
| 4,352,884 | 10/1982 | Nakashima | 435/180 |
| 4,362,620 | 12/1982 | Lemieux et al. | 536/116 |
| 4,486,376 | 12/1984 | Makino et al. | 210/500.38 |
| 4,557,925 | 12/1985 | Lindahl et al. | 424/482 |
| 4,627,992 | 12/1986 | Badenhop et al. | 264/49 |
| 4,629,619 | 12/1986 | Lindahl et al. | 424/482 |
| 4,629,620 | 12/1986 | Lindahl et al. | 424/482 |
| 4,634,604 | 1/1987 | Tlùstakova et al. | 210/198.2 |
| 4,663,163 | 5/1987 | Hou et al. | 210/635 |
| 4,673,734 | 6/1987 | Tayo et al. | 530/364 |
| 4,681,870 | 7/1987 | Balint, Jr. et al. | 502/403 |
| 4,724,207 | 2/1988 | Hou et al. | 435/180 |
| 4,761,232 | 8/1988 | Bright | 210/500.42 |
| 4,772,391 | 9/1988 | Baker et al. | 210/490 |
| 4,781,838 | 11/1988 | Crassous et al. | 502/402 |
| 4,824,678 | 4/1989 | Lindahl et al. | 424/473 |

OTHER PUBLICATIONS

Bannett et al., *Transplantation* (1987) 43:909-910.

Hasirci et al., *J. Biomed. Materials Res.* (1986) 20:963-970.

Neumann et al., "Biocompatible Polymers, Metals, and Composites" (1983) Szycher, editor; Technomic, PA pp. 53-80.

Thomas et al., "Biological and Biomechanical Performance of Biomaterials" (1986) Christel et al., eds. Elsevier, Amsterdam pp. 379-383.

Zingg et al., *Biomaterials* (1981) 2:156-158.

Strong et al., *Anal. Biomed. Eng.* (1982) 10:71-82.

Boardman, *J. Chromatog.* (1959) 2:388-397.

FIG. 1

Table I

Structure of Blood Groups A and B Specific Synthetic Oligosaccharides

| Structure | A Type | B Type |
|---|---|---|
| I. | αGalNAc (1-3) βGal<br>\|(1-2)<br>αFuc | αGal (1-3) βGal<br>\|(1-2)<br>αFuc |
| II. | αGalNAc (1-3) βGal (1-3) βGlcNAc<br>\|(1-2)<br>αFuc | αGal (1-3) βGal (1-3) βGlcNAc<br>\|(1-2)<br>αFuc |
| III. | αGalNAc (1-3) βGal (1-4) βGlcNAc<br>\|(1-2)<br>αFuc | αGal (1-3) βGal (1-4) βGlcNAc<br>\|(1-2)<br>αFuc |
| IV. | αGalNAc (1-3) βGal (1-3) αGalNAc<br>\|(1-2)<br>αFuc | αGal (1-3) βGal (1-3) αGalNAc<br>\|(1-2)<br>αFuc |
| V. | αGalNAc (1-3) βGal (1-3) βGalNAc<br>\|(1-2)<br>αFuc | αGal (1-3) βGal (1-3) βGalNAc<br>\|(1-2)<br>αFuc |
| VI. | αGalNAc (1-3) βGal (1-4) βGlc<br>\|(1-2)<br>αFuc | αGal (1-3) βGal (1-4) βGlc<br>\|(1-2)<br>αFuc |
| VII. | αGalNAc (1-3) βGal (1-3) βGal<br>\|(1-2)<br>αFuc | αGal (1-3) βGal (1-3) βGal<br>\|(1-2)<br>αFuc |

Table 1

| Wash Volume (L) | Number of ≥ 25μm particles/ml from samples under conditions (a) | | | (g) | (h) | |
|---|---|---|---|---|---|---|
| | CF2-11A | CF2-12 28% PEG | CF2-16 1% PEG | CF2-14A 4% PEG | | |
| Saline | 0-4 | 0-4 | 0-2 | 0 | 0-6 | 0-1 |
| 0 | 0-4 | 0-12 | 0-4 | 0-8 | 0-2 | 1-8 |
| 1 | 0 | 0-2 | 0-2 | 2 | 0-1 | 0-1 |
| 2 | 0 | 0-2 | 0-6 | 0-2 | 0-1 | 0-1 |
| 3 | 0 | 0-2 | 0-4 | 0-4 | 0-1 | 0-1 |
| 4 | 0-2 | 0-2 | 0-2 | 0-2 | 0 | 0-2 |
| 5 | 0-4 | 0-2 | 0-2 | 0-2 | 0-1 | 0-1 |
| 6 | 0 | 0-4 | 0 | 0-4 | 0 | 0-1 |
| 7 | 0-2 | 0 | 0-2 | 0 | 0 | 0-2 |
| 8 | 0-2 | 0 | 0-2 | 0-4 | 0-1 | 0 |
| 9 | 0-4 | 0-2 | 2 | 0 | 0 | 0-1 |
| 10 | 2-4 | 0 | 0-2 | 0 | 0 | 0-2 |

Note: All results represent counts from triplicate samples.

Figure 5A

Table 2

|  | ≥ 5 μm Particles/mL in Wash-Volumes at | | | |
|---|---|---|---|---|
| Sampling Conditions | 0 mL | 100 mL | 1 L | 2-10 L |
| (b) for CF2-16 (1% PEG) | 0 | 0 | 0 | |
| (c) " | 0 | 0 | 0 | |
| (d) " | 0 | 0 | 0 | |
| (e) " | .82 | 0 | 0 | |
| (f) " | 48 | 0 | 0 | |
| (g) for CF2-14A (4% PEG) | 2257 | 0 | 0 | 0 |
| (h) " | 42 | | 0 | 0 |

Notes: All results represent average of counts from triplicate samples.

Figure 5B

AFFINITY SUPPORTS FOR HEMOPERFUSION

This application is a division, of allowed application Ser. No. 07/270,950 filed, Nov. 9, 1988.

TECHNICAL FIELD

The invention relates to the field of extracorporeal treatment of body fluids and affinity chromatography. In particular, it concerns particulate supports with protective membrane-type coatings suitable both for hemoperfusion and for a range of less exacting chromatographic and sample treatment techniques.

BACKGROUND ART

Convenient chromatographic supports which are stable, have high capacity, and have low nonspecific adsorption, have long been sought. However, this combination of properties is singularly difficult to achieve. Single-substance supports such as charcoal or synthetic polymers are nonspecific, and apparently cannot be made with both high capacity and stability. Hybrid gels, such as that obtained by impregnating porous silica with DEAE dextran, also suffer these defects.

A number of hybrid supports of this nature have been disclosed, for example, in U.S. Pat. No. 4,673,734, directed to a mineral support impregnated with aminated polysaccharide; U.S. Pat. No. 3,577,226, describing polymerization and formation of a cross-linked polymer in the pores of silica gel in situ; Boardman, N. K., *J Chromatog* (1959) 2:388–389, which describes the formation of a thin layer of resin in the cavity of a porous support such as celite; and U.S. Pat. No. 3,878,092, which also describes a polymeric-coated silica.

Uncoated forms of silica and porous glass, while providing a high porosity and flow rate, are susceptible to degradation and nonspecific adsorption of proteins because of silanol groups at the surface. In order to overcome these disadvantages, hydrophilic polymeric coatings involving silane coupling agents have also been disclosed. For example, U.S. Pat. Nos. 3,983,299 and 4,029,583 describe glycidoxypropyl trimethoxysilane attached to a silica support. However, the adhesion qualities of the coating are poor.

U.S. Pat. No. 4,332,694 describes the combination of a reactive epoxy with an inorganic silica support. U.S. Pat. No. 4,352,884 describes coating of inorganic materials with a copolymer of hydrophilic acrylate or methacrylate along with a copolymerizable carboxylic acid or amine, and a cross-linking agent, a procedure which resulted in insufficient binding to the underlying substrate. U.S. Pat. No. 3,795,313 describes a siliceous support coated with a methacryloxysilane; U.S. Pat. No. 3,808,125 describes a silica support chemically bonded to a copolymer made from a coupling agent polymerized onto a polymeric backbone. In a different approach, U.S. Pat. No. 4,070,348 describes copolymers of glycidyl and amino-containing acrylates which are covalently modified with specific ligands, such as enzymes or proteins.

European patent application No. 0172579, published Feb. 26, 1986 and the U.S. Pat. No. 4,724,207, describe a modified silica support covalently bonded to a synthetic copolymer which contains a polymer which can be covalently coupled directly to the silica copolymerized with a material which contains either an ionizable group, a hydrophobic material, or a group capable of binding an affinity ligand. A related U.S. Pat. No. 4,663,163 describes and claims similarly modified polysaccharide supports. Thus, these supports use a subsequently cross-linked polymeric coating as a matrix to contain the specificity-conferring derivatization and as a link to bind this material to the particulate organic or inorganic support.

None of the foregoing-described chromatographic supports would be suitable for use in hemoperfusion, either because the flow properties are inadequate, because the supports are too unstable, or because nonspecific binding is too prevalent. The foregoing approaches may also result in hydrogels associated with the acrylic polymers which are inherently disadvantageous as poorly adhering and unduly significant in modifying the mechanical properties of the basic particles. For example, polyacrylic hydrogels have calculated average pore radii of only 4–10 angstroms (Refojo, M. F., *J Ap Polym Sci* (1965) 9:3417; White, M. L., *J Phys Chem* (1960) 64:1563. Such pore sizes effectively exclude even small plasma proteins such as albumin (158 Å×38 Å) and gamma globulin (235 Å×44 Å).

For the foregoing reasons, the above-referenced chromatographic supports are inappropriate for ex vivo treatment of biological fluids such as blood or plasma. Suitability for such use requires high dimensional stability, without any particulate release, high efficiency and capacity, and biocompatibility, including lack of nonspecific adsorption. In presently practiced techniques, nonspecific adsorbents, such as activated charcoal, ion exchangers or resins, have been used for plasma perfusion, which is easier to conduct than hemoperfusion but requires additional equipment to separate cells from plasma and may also involve filtration of treated plasma. Attempts to perform specific removal of blood components have been reported, such as the passage of blood through a tube coated with a specific immunoligand (Schenkein et al, *J Clin Invest* (1971) 50:1964; Lyle et al, *J Immunol* (1974) 113:517). Terman et al, *Clin Exp Immunol* (1977) 28:180, describes an encapsulated sorbent coupled to nylon and used as column, Terman et al, *New Eng J Med* (1981) 305:1195–1200, describes the use of protein A bound to charcoal-collodion to treat solid tumors, and Besa et al, *Am J Med* (1981) 71:1035, describes a stabilized protein A to remove serum IgG in an autoimmune therapy. U.S. Pat. No. 4,681,870 discloses the use of a protein A silica immunosorbent to remove IgG from biological fluids, a process which suffers from the disadvantage of the release of "fines" during the ex vivo treatment. Messaikeh et al, "Biological and Biomechanical Performance of Biomaterials" (1986), Christel et al, eds, Elsevier, Amsterdam, pp. 321–326, describes use of derivatives of polystyrene to remove Factor VIII:C ex vivo. Margel et al, *Ap Biochem Biotechnol* (1986) 12:37–66, describes the use of derivatized cross-linked agarose polyacrolein microspheric beads ("agarose acrobeads") for specific hemoperfusion.

The use of specific affinity ligands coupled directly to an inorganic support as a matrix for selective removal of materials from the plasma or blood was described by Bensinger et al in a series of articles appearing in *Transfusion* (1981) 21:335–342; *New Eng J Med* (1981) 304:160–162; *J Clin Apheresis* (1982) 1:2–5; and *Vox Sanq* (1985) 48:357–361. In the latest of these disclosures, the immunoadsorbent was thinly coated with collodion applied by the method described by Chang, *Trans Am Soc Artif Int Organs* (1980) 26:546–549 and the related U.S. Pat. No. 3,725,113, but the thin collodion coating did not prevent the release of fines. Hydrophilic coatings of nonspecific supports are described. Others have used similar columns for removal of antibodies from human plasma (Osterwalder et al, *Blut* (1986) 53:379-390; Bussel et al, *Plasma Ther Transfus Technol* (1985) 6:461-464) and from whole blood (Raja et al, ibid (1986) 22:102-103, and Bannett et al, *Transplantation* (1987) 43:909-910). Attempts to coat adsorbents also include the use of glow discharge to polymerize hexamethyldisiloxane on the surface of activated charcoal granule for hemoperfusion (Hasirci and Akovali, *J Biomed Mater Res* (1986) 20:963-970), again failing to prevent the release of fines.

An additional problem is non-specific adsorption to the support. The adhesion of various materials to polymeric substances has been studied. A review of biocompatibility of various polymers is found in Neumann et al, in "Biocompatible Polymers, Metals and Composites" (1983) (Szycher, ed), Technomic, PA. For example, polystyrene has been shown to be a poor adherent for cells (Thomas et al, in "Biological and Biomechanical Performance of Biomaterials" (supra)). Platelet adhesion does not seem to depend on surface smoothness or roughness (Zingg et al, *Biomaterials* (1981) 2:156-158); however, for hydrophobic surfaces surface roughness does affect cell adhesion under flow conditions (Strong et al, *Anal Biomed Engg* (1982) 10:71-82).

The present invention provides a process for providing a controlled pore coating with membrane-type physical properties conferring integrity and mechanical strength, which is biocompatible for use in protecting affinity supports to prevent the release of fines. The coating is thus consistent with suitable mechanical properties of membranes, and is of appropriate porosity to accommodate the penetration of blood proteins such as antibodies or other materials for which an affinity ligand attached to the support is reactive.

DISCLOSURE OF THE INVENTION

A hemoperfusion device containing a novel affinity adsorbent is provided for the selective removal of specific substances from blood. The device overcomes the limitations of prior art chromatographic supports intended for extracorporeal immunoadsorption in clinical applications. The supports are also useful for large-scale separation and purification of biological macromolecules, based on affinity chromatographic techniques.

The specific removal of unwanted substances from the blood circulation by extracorporeal hemoperfusion has profound medical significance as it is far more desirable and convenient than plasmapheresis. When appropriate affinity ligands are employed, only substances with specificity for binding to the ligand are removed. The invention provides a support over which the whole blood (or plasma) can be safely circulated and then returned directly into the human body. The supports are thus "biocompatible", i.e., these supports do not adversely affect any blood components other than that specifically targeted. In addition, the supports resist cellular and platelet adhesion, and prevent the release of fines, which could otherwise lead to harmful embolism.

The adsorbent matrix of the invention is comprised of silica or other inert particles to which an affinity ligand is attached, wherein the resulting derivatized support is modified by a membrane-type coating. The adsorbent matrix has properties suitable for selective removal of antibodies or other undesirable substances directly from bloodstream or plasma by extracorporeal immunoadsorption. The coating involves formation of ultrathin, porous film of the synthetic membrane-type, obtained by a technique similar to the phase inversion method commonly employed in formation of membranes per se.

Because they more easily produce integral membranes, hydrophobic polymers to obtain the membrane-type coating are preferred. In such instances, it may be necessary to include, along with the polymer, a dissolved compatible pore-controlling component in an amount 0.5-5% of the weight of said polymer. The solvent is then removed to form the desired biocompatible membrane-type coating, which coating has a pore size equal to or greater than 20 angstroms. More hydrophilic polymer coatings may not require the pore-controlling component. When coated with a membrane-type coating, the support shows stability with respect to fines, at least after further washing as needed to remove preliminary fine components. The invention is also directed to the polymeric membrane-coated matrix either underivatized, or derivatized to an affinity ligand.

Thus, in one aspect, the invention is directed to a method to coat specific-affinity adsorbents which method comprises preparing a suspension of a particulate solid inert support (which is underivatized or derivatized with the affinity ligand) wherein the suspension is prepared in a solvent containing dissolved polymer in an amount of 0.1-1% of the weight of matrix, under conditions wherein, and followed by steps whereby, the support is provided with a membrane-type coating to the polymer, said membrane-type coating having the physical and mechanical properties of an integral membrane, but wherein the membrane has pores of sufficient size to permit access of the substances to be adsorbed to the affinity ligand. Accordingly, the pore size should be at least 20 angstroms.

In another aspect, the invention relates to a device containing the coated matrix of the invention and to methods of conducting extracorporeal perfusion techniques with body fluids employing it. In particular, the invention is directed to a method of hemoperfusion using the coated supports of the invention.

BRIEF DESCRIPTION OF THE DRAWINGS

FIG. 2 shows several affinity ligands useful in the invention method.

MODES OF CARRYING OUT THE INVENTION

A novel immunoadsorbent material is provided for, for example, the selective removal of specific substances such as antibodies from the bloodstream. Blood is withdrawn from a patient, circulated as whole blood through the membrane-coated support of the invention to remove the unwanted substance and the treated blood returned directly to the patient. Alternatively, the blood cells may be separated from the whole blood before treatment; the separated plasma is then treated by passing it over the membrane-coated support and returning it to the patient. The separated blood cells can also be reinfused into the patient directly or after mixing with the treated plasma.

The membrane-coated support of the invention, when in use, generally contains an affinity ligand. The ligand may be chosen from, for example, chemically synthesized structures such as oligosaccharide determinants for human blood groups, and can be covalently attached, directly or using a linker, or non-covalently adsorbed preferably using a suitable carrier molecule to a supporting particulate such as silica particles, porous glass, etc. The immunoadsorbent thus obtained is modified by the membrane type coating technique of the invention to impart properties more suitable for whole blood hemoperfusion (or for use generally), by preventing fines, but permitting the passage of whole blood containing the component to be removed, and permitting the component to reach the specific ligand.

A. DEFINITIONS

As used herein, "biocompatible membrane-type coating" refers to a material which has been coated to an inert support or to a functionalized or an affinity derivatized support using the method of the invention and which is, from the standpoint of composition, a synthetic or naturally derived polymeric material which is chemically inert with respect to physiological substances, and is biocompatible when used in contact with extracorporeal fluids, including blood. It is believed that biocompatibility may be enhanced by formation of a secondary albumin coating when in use under certain conditions.

"Pore-controlling component" refers to a material which is soluble in both the solvent used in the coating preparation, and the gelation/wetting/leaching medium which follows the solvent evaporation step described below. The pore-controlling component is also inert with regard to forming a coating on the derivatized support. The pore-controlling component is a nonsolvent or polymer-swelling agent whose function is to control the size and/or number of pores, therefore wettability and stability of the coated matrix. Examples include, for example, low molecular weight polymers such as polyethylene glycol (PEG), especially MW 300–20,000, and polypropylene glycol, polyvinyl alcohol, polyvinyl pyrrolidone (PVP), or other low molecular weight, relatively hydrophilic polymers. Also usable are nonionic detergents such as Tween-20, Triton-X, various Solulans, electrolytes and the like.

"Inert support" refers to the particulate inert material to which the coating polymer will be applied.

"Derivatized" support refers to the inert support which has conjugated thereto an affinity ligand. The ligand may be directly bound covalently (or noncovalently) to the support, or a linker and sometimes a carrier may be employed.

"Functionalized" support refers to the inert support to which only a linker moiety, or a moiety which provides a functional group for further conjugation (e.g., a succinyl group to provide a carboxyl) is attached. Functionalized support refers both to supports coated with the membrane-type coating film of the invention, or not coated.

"Underivatized support" refers to support lacking added linkers or affinity ligand. To fit the definition of "underivatized support" it also does not matter whether the invention coating has or has not been applied.

"Linker" refers to a moiety which serves to space the affinity ligand from the particulate support. The distinction between a "linker" and a general moiety which provides a functional group for further conjugation is not precise, nor is such precision important. Affinity ligands can be, and often are, provided with linkers or "linking arms" before they are conjugated to support; the linker will contain a functional group capable of binding to a functional group either native to the support or provided by an additional conjugating moiety.

B. MATERIALS

The invention provides a method to obtain a coated, protected affinity adsorbent which is safe for use in hemoperfusion, as well as in the less demanding procedures of plasmaperfusion and ordinary affinity chromatography.

THE SUPPORT

The affinity matrix can be any derivatized particulate having a specific ligand conjugated to or otherwise bound to the solid support particles.

For preparation of invention substrates, a wide variety of such solid particulate supports has been described, as set forth in the Background section above. The solid support particles useful in the invention are of a variety of inert materials in particulate form, including various silica derivatives such as silica powder, synthetic silicates such as porous glass, biogenic silicates such as diatomaceous earth, silicatecontaining minerals such as kaolinite, and so forth. Other suitable supports may include synthetic resins or particulate polymers such as polystyrenes, polypropylenes, polysaccharides, and so forth, including those useful as coating polymers, as set forth below, or other commonly used chromatographic supports such as alumina. Silaceous materials are particularly preferred. Particularly preferred is calcined diatomaceous earth of the cristobollite type, which contains surface hydroxy groups; these are convenient for covalent attachment of ligands. Mesh sizes can vary according to intended use from about 150 to 12; for hemoperfus n, 60/30 mesh is particularly preferred.

AFFINITY LIGANDS

The solid support (coated as described below, or uncoated) is directly conjugated or otherwise covalently or noncovalently bound to an affinity ligand—i.e., a material which has a specificity for a component of the sample to be subjected to treatment with the affinity support. Such ligands include immunoglobulins, fragments of immunoglobulins such as Fab, F(ab')$_2$ or Fab' fragments, specifically interacting materials such as biotin and avidin, bioreactive proteins such as protamine or enzymes such as heparinase, nucleotide sequences, glycosaminoglycans such as heparin, and carbohydrate moieties which represent antigenic or specifically reacting domains of various biological materials. Some ligands, especially the carbohydrate moieties, may be provided as conjugates, for example, with proteins. In the specific adsorbents of the invention, this ligand is coated passively or is conjugated to the solid support either directly, or through a linker, before or after the polymeric coating is applied. The linker is typically an organic bifunctional moiety of appropriate length which serves simply to distance the ligand from the surface of the solid support. Suitable ligands and linkers are those disclosed, for example, in U.S. Pat. Nos. 4,137,401, 4,238,473 and 4,362,720.

The membrane-type coating which characterizes the affinity matrices of the invention is an integral film which has the physical and mechanical properties of a single membrane, but which contains pores of 20 angstroms or more so that materials in the fluid to be treated will have ready access to the affinity ligand attached to the support. The membrane itself is formed from a polymer so that the film is integral over the particle but leaves the required pores in the surface. A variety of polymers can be employed, as set forth below, but the process followed and conditions used to achieve the required pore size and the integral film will depend on the nature of the polymer chosen.

MEMBRANE-TYPE COATINGS

Hydrophobic polymers are preferred, as integral membranes are more easily obtained than with more hydrophilic materials. Because the final steps in the coating and adsorption processes are conducted in aqueous media, hydrophilic polymers tend to form coatings which "fall apart" unless the membrane formation is very carefully controlled and managed. Thus, e.g., the prior art collodion coatings of Chang (supra) do not fall within the scope of the invention, as they are applied without attention to parameters that assure integral membrane formation nor do they use the desired hydrophobic polymers.

If hydrophobic polymers are used, the formation of an integral membrane-type coating is relatively facile—it is required only to use the proper ratio of polymer to support and to evaporate the solvent carefully. In order to assure formation of appropriate number and size of pores, it may be required, when hydrophobic polymers are used, to include a "pore-controlling substance". This material is typically a low MW polymer and must be soluble in the solvent used for coating and in the gelation/wetting/leaching medium which effects, among other things, preliminary removal of fines.

Exemplary of polymers which can be used as the biocompatible membrane-type coating in the method of the invention include hydrophobic materials, such as polystyrenes, polyetherurethanes, polysulfones, fluorinated or chlorinated polymers such as polyvinyl chloride, polyethylenes and polypropylenes, polycarbonates and polyesters. The hydrophobic polymers also include other polyolefins, such as polybutadiene, polydichlorobutadiene, polyisoprene, polychloroprene, polyvinylidene halides, polyvinylidene carbonate, and polyfluorinated ethylenes. Copolymers are also useful as coatings, such as styrene-butadiene copolymer or copolymer of α-methylstyrene and dimethylsiloxane. Other polymers useful in the invention are synthetic or natural rubbers and polysiloxanes (silicone polymers) containing aliphatic or aromatic moieties such as polydimethylsiloxane, polyphenylmethylsiloxane, and polytrifluoropropylmethyl siloxane. Also useful are polyacrylonitriles or acrylonitrile-containing copolymers, such as poly α-chloroacrylonitrile copolymers; polyesters, including polylactams and polyarylates; polyalkylacrylates and polyalkylmethacrylate; alkyd or terpinoid resins; polysulfones, including aliphatic-containing polysulfonates, polyalkylene polysulfates. More hydrophilic polymers include polyalkylene glycols, such as polyethylene glycol and polypropylene glycol, of relatively high molecular weight; polyarylene oxides; nylons, polyvinyl alcohols, and polyphosphates, such as polyethylene methylphosphate, and the like, can also be used. For all of the above, copolymers, including block interpolymers, and grafts and blends can be employed. Suitable biologically derived polymers include polyhydroxy materials such as cellulosic polymers, proteins, such as serum albumin and collagen, glycosaminoglycans, and the like.

The polymers, especially polysiloxanes, polyhydroxy materials, and proteins, may be cross-linked either after the coating is applied or during the in situ formation of the coating.

The performance of the matrix for adsorption of larger moieties reactive with the affinity ligand and its wettability are enhanced by the inclusion of pore-controlling components in some circumstances as further described below.

If hydrophilic polymer coatings are used, it is inadvisable to add a pore-controlling component since integrity of the membrane is already difficult to achieve. For hydrophobic polymers, addition of a pore-controlling component may not be needed if the interaction of the ligand and substance to be adsorbed involves sufficiently small-sized moieties. For example, using a polystyrene coating, pores of sufficient size to permit IgM to be adsorbed to an affinity ligand conjugated to support are formed without this additional component.

C. THE COATING PROCESS

The supports of the invention are characterized by having a membrane-type coating which is integral over the surface of the membrane and which contains pores of the correct size. The process to obtain this coating is critical to provide the desired characteristics wherein the number and size of the pores in the membrane-type coating film are controlled, and the wettability and stability of the support are controlled also by the membrane. In the process for preparing this membrane-type coating, therefore, the composition of the coating solution, including the nature and concentration of the polymer used and the conditions of evaporation and gelation, including the composition and nature of the gelation/leaching bath medium are critical to obtaining these results. Methods to obtain integral membranes in general are known in the membrane-forming art, and these methods are applied to the affinity supports of the invention.

The derivatized support is coated with a membrane-type film of the biocompatible polymer with pores of at least 20 Å according to a method appropriate for the choice of polymers. The coating procedure can be conducted before or after functionalization or before or after derivatization of the support to the specific ligand, since the pore size of the membrane-type coating can be controlled in the method of the invention, and can thus be adjusted to permit subsequent derivatization of the support.

In the invention method, the protective coating membrane is thus applied to the derivatized, functionalized, or underivatized support by supplying the polymer coating in a solvent medium which contains an amount of polymer appropriate to obtain the desired thickness of an integral film. This amount is a weight of polymer which is 0.1–1% of the weight of particulate support, for particles of 12–150 mesh. After thorough mixing and incubation for a suitable period, typically 15–30 min, the solvent is evaporated under vacuum until the polymer-coated particles are dry. As is understood in the art, the polymer may be cross-linked (or not) during the coating process, or immediately thereafter, preferably before evaporation of solvent. The dried particles are then wetted in a gelation/wetting/leaching medium, typically an aqueous medium, to effect gelation of polymer, leaching of nonintegral components, and to remove fines already present. By adjusting the parameters of polymer solution composition, temperature, time of incubation, rate of solvent evaporation, gelation conditions etc., to mimic those typically used in the formation of thin porous membranes, the resulting film has physical integrity.

If the polymer is relatively hydrophilic, such as cellulose acetate, nylon, serum albumins, and the like, pore formation of adequate size may occur automatically. It is more difficult, however, to achieve an integral coating. When hydrophobic polymers, such as polystyrene and polysulfone, are used, the process may have to be modified in order for the coating to have pores of 20 angstroms or more. This is achieved through the addition of a pore-controlling component to the coating mixture. Similar to the procedure above, when a pore-controlling component in effective concentration is present, after incubation with agitation for a suitable time period, the solvent is evaporated, and the dried solid is resuspended in a gelation/wetting/leaching aqueous medium to remove fines, including uncoated polymeric gels, pore-controlling nonsolvent component, and any residual solvent.

Typically, the process is conducted by suspending the solid support in a solution containing both polymer and pore-controlling component. The concentration of polymer represents 0.1–1%, preferably 0.5%, of the weight of solid support suspended; the pore-controlling component is present in an amount of 0.5–5%, preferably about 1% of the weight of the added biocompatible polymer; hence it is present at a substantially lower concentration. The choice of pore-controlling component depends, of course, upon the choice of polymer, the appropriate solvent for polymer, as well as the gelation/wetting/leaching medium. The pore-controlling component must be compatible with the polymer and must be soluble in both solvent and with the gelation/wetting/leaching medium.

In a typical protocol, the polymeric material is dissolved at a concentration of approximately 2 g/l of a suitable solvent with warming if necessary, and the appropriate amount, typically around 20 mg (about 0.5–5% of the weight of the polymer which will form the membrane coat) of the pore-controlling component is added while stirring. When both components are dissolved, the dried solid support, approximately 400 g/l, or 100–1000 times the weight of the polymer which will form the membrane coat, is suspended by gentle agitation in the solution. The suspension is then gently agitated for a suitable time, approximately 15–30 min, and the polymer may then be cross-linked (or not) before evaporation of the solvent under vacuum. Both agitation and evaporation are conveniently conducted in a rotovap. The temperature may be increased during the last stages of evaporation, and the coated matrix should appear completely dry.

The coated matrix is then cooled gradually to room temperature and suspended in a gelation/wetting/leaching medium, typically a water bath which may contain other components helpful in controlling pore size, such as alcohols (e.g., ethanol), acids (e.g., sulfuric acid), and the like, depending on the nature of polymer, for a suitable time, typically 1–2 hr, preferably under ambient conditions or at temperatures of about 4°–40° C., depending on the polymer. The matrix, if properly coated, should not show visible gelation or precipitation during this wetting process.

Whether a pore-controlling component has been included or not, the suspended matrix is then washed thoroughly with leaching medium such as water in order to eliminate any fine particles or traces of the coating mixture, including any pore-controlling component or swelling agent and residual solvent.

The washed matrix is then dried by suction, and then by heating to about 60° C. to constant weight.

If the matrix has not yet been derivatized to the specific ligand, the derivatization process is then conducted, appropriately, on the suspended membrane-coated matrix.

D. CHARACTERISTICS OF THE COATED MATRIX

The coated matrices of the invention are of suitable capacity, porosity, handling characteristics, stability, and specificity, if desired, to be useful, not only in standard chromatographic procedures, but also in extracorporeal treatment of biological fluids. Accordingly, the materials are biocompatible in that they are capable of effecting the required separation or removal without disturbing any accompanying biological components.

On a molecular level, the materials for use in affinity chromatography or perfusion can be described as particulate solid supports to which are adsorbed or covalently bound, either directly or through linking arms, an appropriate affinity ligand. The entire derivatized support is coated with a thin integral membrane-type film of polymeric material having a pore size appropriate to the material for which binding is intended. Suitable pore sizes are of the order of 20 angstroms or greater for removal of specific substances such as proteins or antibodies from biological fluids. The materials of the invention are characterized by the attachment of the affinity ligands to the particulate support, rather than to a polymer coating, and by the porous, thin, enveloping coat. (Also included in the invention are comparably coated supports which have not been derivatized to affinity ligand. These are intermediates in the formation of the matrices of the invention or can be used in non-specific procedures.)

E. USE OF THE COATED SUPPORTS

Figure 1:
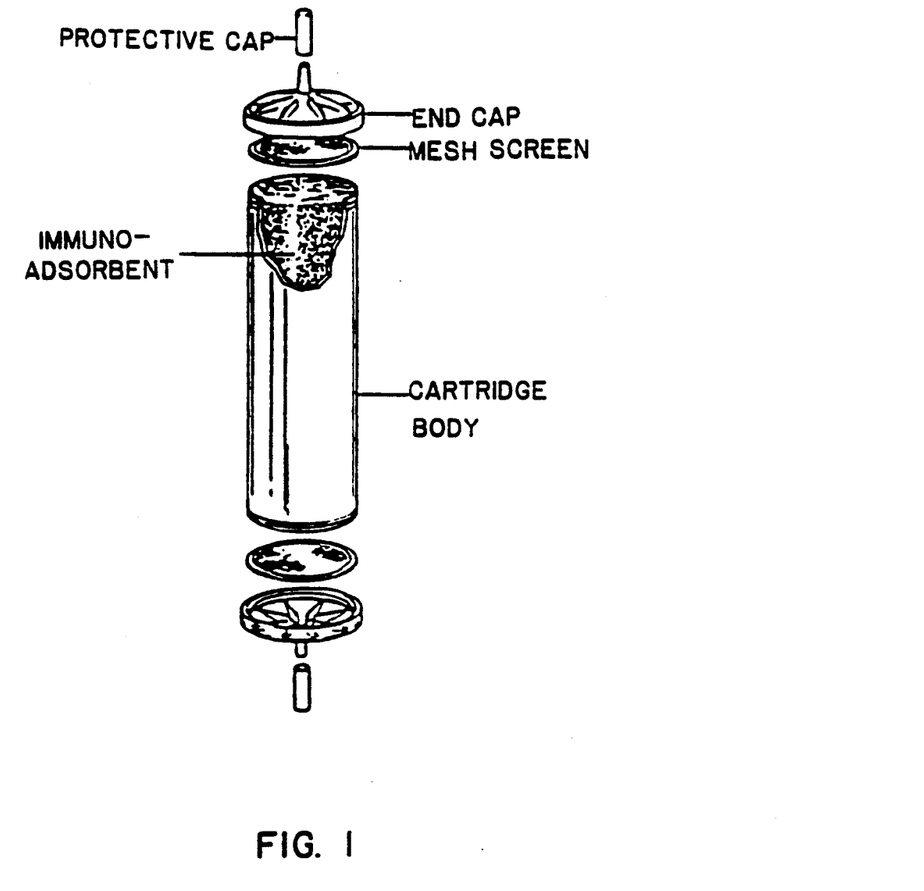
FIG. 1 shows an illustrative cartridge arrangement for use in hemoperfusion using the immunoadsorbents of the invention.

In general, the affinity matrices of the invention are used in a manner similar to affinity chromatographic supports for standard chromatographic procedures, as well as for extracorporeal perfusion of biological fluids such as plasma and blood. For this latter purpose, a preferred arrangement utilizes a cartridge for packaging of the matrix typified by that shown in FIG. 1. As shown, the cartridge consists of a cylindrical body, a pair of end caps, a pair of mesh screens at either end, and protective cap plugs. A variety of similar designs can be used, but the materials of the cartridge components must themselves be biocompatible, such as polyethylene, teflon or lexan polycarbonates. The loaded cartridge is assembled by placing a mesh screen over one end of the cylinder and fitting an end cap over the screen. The cylinder is then filled with the affinity matrix of the invention, and assembly is completed by placing the other mesh screen and fitting the other end cap in place. Generally, the packing is done under sterile conditions or the cartridge together with its contents can be sterilized after packing, for example, by ethylene oxide sterilization. The affinity matrix is then wetted by pumping in pyrogen-free normal saline and washing to insure the removal of any small particles that have been dislodged from the matrix or left during preparation.

The cartridge is then filled with a 1% solution of human serum albumin in normal saline and stored at 4° C. When ready for use, the cartridge is washed with 0.9% sodium chloride solution to which has been added a suitable anticoagulant, such as ACD-A containing heparin in an effective amount. For a 250 ml cartridge, for example, this is approximately 1 l of the sodium chloride solution to which 150 ml of ACD-A containing 6,000 units of heparin has been added.

In use, the subject's blood or plasma is passed through the cartridge by placing a shunt, e.g., a loop of plastic medical grade tubing, in the patient's arm and circulating the blood through the cartridge with a direct return to the patient. Alternatively, the blood can be circulated through the tubing by a continuous-flow blood separator such as an IBM Model 2997 or a semipermeable membrane separator to allow passage of plasma separated from the cellular components. The plasma is then passed through the cartridge and returned directly, or after remixing with cells, to the subject.

The coated haptenized supports can also be used for purification of desired blood components or ligands from other biological fluids. The biological fluid is tumbled with the appropriate specific coated adsorbent at a temperature of 4° C.-room temperature, and the adsorbed biological material eluted using procedures appropriate to the particular ligand. For elution of antibodies; for example, 2% ammonia in 0.15M saline or 0.2M acetic acid adjusted to pH 2, are satisfactory. Other eluants which may be employed are 1% ammonia in saline, 0.2M glycine hydrochloride, various chaotropic ions, and 0.1M saccharide solution.

For removal of anti-A or anti-B antibodies, approximately 25 mg of the matrix prepared as in Example 1 below is sufficient to remove all antibodies from 1 ml of antisera of saline titer 1/64.

The matrix may be reused several times without loss of activity if reequilibrated with starting buffer before application of the new sample. For purification, as opposed to hemoperfusion, smaller particle size (100/120 mesh) is preferred.

F. EXAMPLES

The following examples are intended to illustrate, but not to limit, the invention. In general, the examples and associated preparation procedures illustrate the attachment of the affinity ligand to the particulate support and the coating of the derivatized, functionalized, or underivatized support with the membrane-type coating of the invention. As stated above, these two aspects of treatment of the solid support can be conducted in any order. Suitable procedures for derivatizing glycoside haptens to the particulate support through linking arms are described in U.S. Pat. Nos. 4,137,401; 4,238,473; and 4,362,720, incorporated herein by reference. Preparation A exemplifies the procedures employed in these issued patents.

PREPARATION A: COUPLING OF TRISACCHARIDES TO AMINOSILATED DIATOMITE

A. Acid-washed diatomaceous earth was aminosilated using the procedure of Westal and Filbert, Meth Enzymol (1974) 34B: 64 and Weetall, Nature (1969) 223: 959–960, as employed in U.S. Pat. Nos. 4,137,401 and 4,238,473, cited above. The synthetic hapten, the 8-azidocarbonyloctyl derivative of the A trisaccharide, IA of FIG. 2, (ATS), as described in the cited patent 4,362,720 (2.31 g) is dissolved in 30 ml dry DMF by stirring in a flask placed in an acetone/dry ice bath under dry conditions. The temperature of the bath is then adjusted to −25° C. and 1.35 ml of 4.55M HCl in 1,4-dioxane is added, followed by 252 µl of t-butyl nitrite. The reaction mixture is stirred for 30 min and 1.2 ml of diisopropylethylamine is added. The azido solution is then added to a suspension of the aminosilated diatomite (3 kg) in 8.4 l of dry acetonitrile at −2° C. with rapid stirring for 30 min and continued slower stirring for 2.5 hr. The resulting haptenated diatomite is allowed to settle and the solvent distilled off under vacuum. Haptenization of the support is verified by the phenol-sulfuric acid method of DuBois et al, *Anal Chem* (1956) 28: 350–356. Typically, a minimum value of 0.35 µmol hapten/g adsorbent is obtained.

Methanol (7.2 l) was added to the dry haptenized diatomite, stirred for 10 min under vacuum, and 0.18 l of acetic anhydride in 1 l methanol is added. The stirring is continued for 1 hr and the reaction mixture left overnight at room temperature. The solvent is removed by draining, and finally distilled under vacuum. The resulting product is washed repeatedly until the O.D. of supernatant, measured at 420 nm in a 1 cm path, is less than 0.1. Four liters saturated bicarbonate solution is added in the second wash cycle to neutralize residual acetic acid. The washed product is dried by vacuum filtration and again washed with 2 l methanol, spread onto stainless steel trays, placed in an oven, and dried at 70° C. overnight. A typical yield is approximately 2.85 kg.

B. The procedure of paragraph A is similarly conducted using, in place of the 8-azidocarbonyloctyl derivative of the A trisaccharide, the corresponding B-trisaccharide, IB of FIG. 2, or the oligosaccharides numbered II–VII in FIG. 2.

EXAMPLE 1

Coating of Trisaccharide A Derivatized Support

A. Polystyrene Coated Derivatized Support Using PEG as Pore-Controlling Component Approximately 6.4 l of trichloroethylene is heated to 45° C. and 14.25 g of polystyrene (m.w. 250,000) is added and dissolved. The pore-controlling component, 0.1425 g of PEG-300 is added while stirring.

The haptenized support of preparation A is then added and the slurry rotated on a rotovap evaporator for 20 min, followed by evaporation of the solvent under vacuum. The temperature is increased to 60° C. and the evaporation of solvent continued until the matrix appears dry.

The matrix is gradually cooled to room temperature and suspended in water for 2 hr under ambient conditions. The matrix is readily wetted, and little or no visible gelation/precipitation occurs. The matrix is then washed thoroughly with water until the supernatant is clear of any gelled polymer and there is no visible indication of fines. The washed matrix is suction-dried on Buchner funnels and dried in an oven at 60° C. for 4 hr or more until constant weight is achieved. The yield of coated product is typically 2.8 kg.

B. Alternate Coatings

Using the same general procedures as set forth in paragraph A of this Example, but substituting other polymers for polystyrene, other or no pore-controlling components for PEG, and an appropriate solvent, the following coated matrices were prepared using 30/60 or 100/120 mesh diatomite derivatized to ATS:

| Designation | Polymer Coating | Pore-Controlling Component | Solvent |
|---|---|---|---|
| CF1-46B | Cellulose acetate (1%) | None | Acetone/water |
| CF1-47C2 | Nylon-66 (1%) | None | Formic acid |
| CF1-47B2 | PSMA (1%) | None | DMF |
| CF1-58A1 | Polystyrene (1%) | None | DMF |
| CF1-58B1 | Polysulfone (1%) | None | DMF |
| CF1-58C2 | Polystyrene (1%) | PVP | TCE |
| CF1-58D2 | Polysulfone (1%) | PVP | DMF |
| CF1-73A2 | BSA (0.2%, cross-linked) | None | Phosphate buffer |
| CF1-73B2 | BSA (0.5%, cross-linked) | None | Phosphate buffer |
| CF1-73C2 | BSA (1.0%, cross-linked) | None | Phosphate buffer |
| CF2-19B | Collodion (0.36%) | None | EtOH |
| CF2-22A1 | Polyether urethane (0.5%) | None | DMF |
| CF2-27A | PDMS (1%) | None | DCM |
| CF2-29 | PVA (1%, cross-linked) | None | Water |

EXAMPLE 2

ATS-Derivatized Diatomite Coated with Human Serum Albumin (HSA)

A solution of 0.40 g HSA (Fraction V, Sigma #A-1653) is prepared by dissolving the protein slowly in a 1 L evaporation flask containing 200 mL water. 80 g of ATS-derivatized diatomite (Preparation A) is added to this solution and the flask is gently rotated for 1 hr. The supernatant is decanted and the matrix is suction-dried on a Buchner funnel, a total of 78.2 mg of protein being recovered in the supernatant. (Alternatively, the matrix may be dried completely under vacuum so that essentially all the protein is deposited onto the matrix.)

The deposited or adsorbed protein is then cross-linked on the coated matrix by adding 200 mL of 1.25% glutaraldehyde solution in 0.033M $KH_2PO_4$. The mixture is stirred at a low speed for 30 mins and then left overnight at room temperature. The settled matrix is decanted and rinsed with 500 mL of water containing 1M NaCl to remove any protein bound only loosely on the matrix. The cross-linking of proteins is evident from the appearance of insoluble films around the flask. However, the amount of protein-films as well as the proteins recovered by rinsing the matrix after glutaraldehyde cross-linking is negligible (about 2 mg) so that the amount of HSA immobilized onto the matrix is about 4 mg/g of matrix, or 5 mg/g when vacuum-dried initially.

The coated matrix is then washed extensively with water (3 L) to remove residual glutaraldehyde and also to remove cloudiness due to fines until visibly clear supernatant is obtained. Finally, the matrix is suction-dried and let stand overnight at room temperature for air-drying until constant weight is achieved. This product is then tested for fines as well as for biological activity.

EXAMPLE 3

Coupling of Antigen ATS-BSA to Amino-silated Diatomite Precoated with Polystyrene Aminosilated diatomite, prepared as in Preparation A, is coated with polystyrene, as described in Example 1. A 1 g sample of the resulting coated, functionalized diatomite is suspended in 10 ml of 0.1M phosphate buffer, pH 7, containing 2.5% glutaraldehyde and incubated for 1 hr at 10° C. with end-over-end rotation, followed by washing extensively with water to remove glutaraldehyde. A solution of 2.675 mg of ATS-BSA conjugate (containing the equivalent of 0.54 μm ATS) is prepared in the same buffer, added to the glutaraldehyde-activated coated matrix, and tumbled overnight at room temperature. The supernatant is decanted and the matrix washed thoroughly with a solution of 1M NaCl in 0.1M phosphate buffer, pH 7.

In one procedure, protein determination of the supernatant and wash showed a loss of 0.43 μmol ATS which was chemically coupled to 1 g of the matrix via glutaraldehyde (BK7-20A). A similar preparation in which ATS-BSA was coupled in the presence of glutaraldehyde gave 0.09 μm ATS/g (BK7-20A1). The conjugated matrix is washed with water and air-dried at room temperature to constant weight.

EXAMPLE 4

Evaluation of Fines

Several procedures were used to determine the level of fine particles removable from matrices of the invention by washing. In an initial rough test, a 0.3 g sample is weighed and placed in a 5 ml test tube, followed by addition of 3 ml of 0.1M PBS. The mixture is allowed to stand for 10 min and the tube then inverted 10 times. After 1 min settling, the supernatant is transferred to a 1 cm cell to measure optical density at 420 nm.

The procedure is also modified to simulate conditions which might be encountered during extracorporeal use of the affinity matrix. Approximately 75 g of matrix is placed in the cartridge shown in FIG. 1, and the cartridge is rotated end over end in a hematology mixer for 1 hr prior to evaluation of fines. Care should be taken that the matrix entirely fills the cartridge. The cartridge is then perfused with 0.9% saline (filtered at 0.2 μm for sterilization) at a flow rate of 40 ml/min using a Masterflex pump. A total of 10 l of saline is perfused through the system and 20 ml samples are collected at every liter washing. A particle count in particle/ml is made for 1) particles which are greater than 5 μm in diameter and 2) particles which are greater than 25 μm in diameter. Counts are determined using a Coulter Counter, Model ZM, with C256 Channelizer. Control counts are performed on saline prior to perfusion and prior to rotation of the cartridge.

Figure 3:
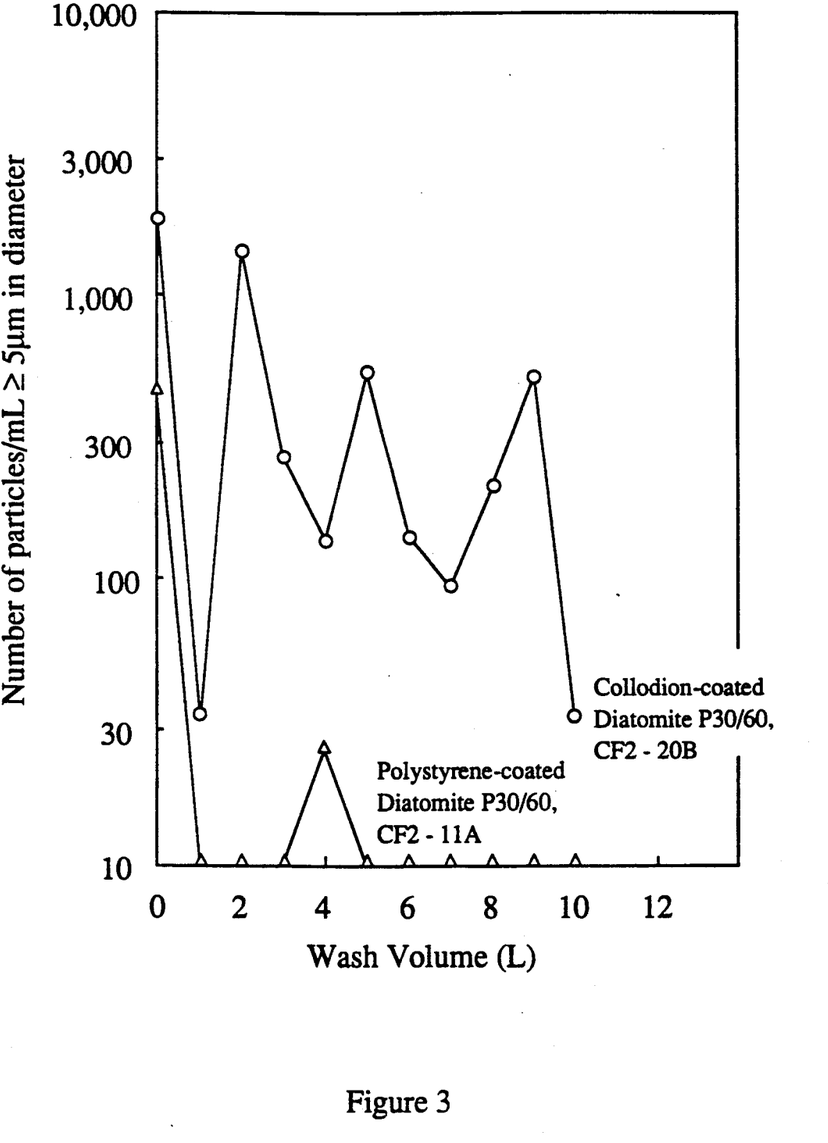
FIGS. 3 and 4 show shedding of fines from immunoadsorbents prepared using coating protocols with varying amounts of pore-controlling component.

FIG. 3 shows the results obtained for fines of diameter greater than 5 μm with control samples—one of which is coated with an integral membrane surrounding the particulate support (a positive control) and the other, a matrix coated with 0.36% collodion, as described by Chang (supra) (a negative control). Both controls are underivatized diatomite, and the procedure of Example 1 is used for the positive control except that the coating solution did not contain any pore-controlling component. As expected, the polystyrene-coated matrix is relatively free of fines as compared to the collodion-coated negative control.

Figure 4:
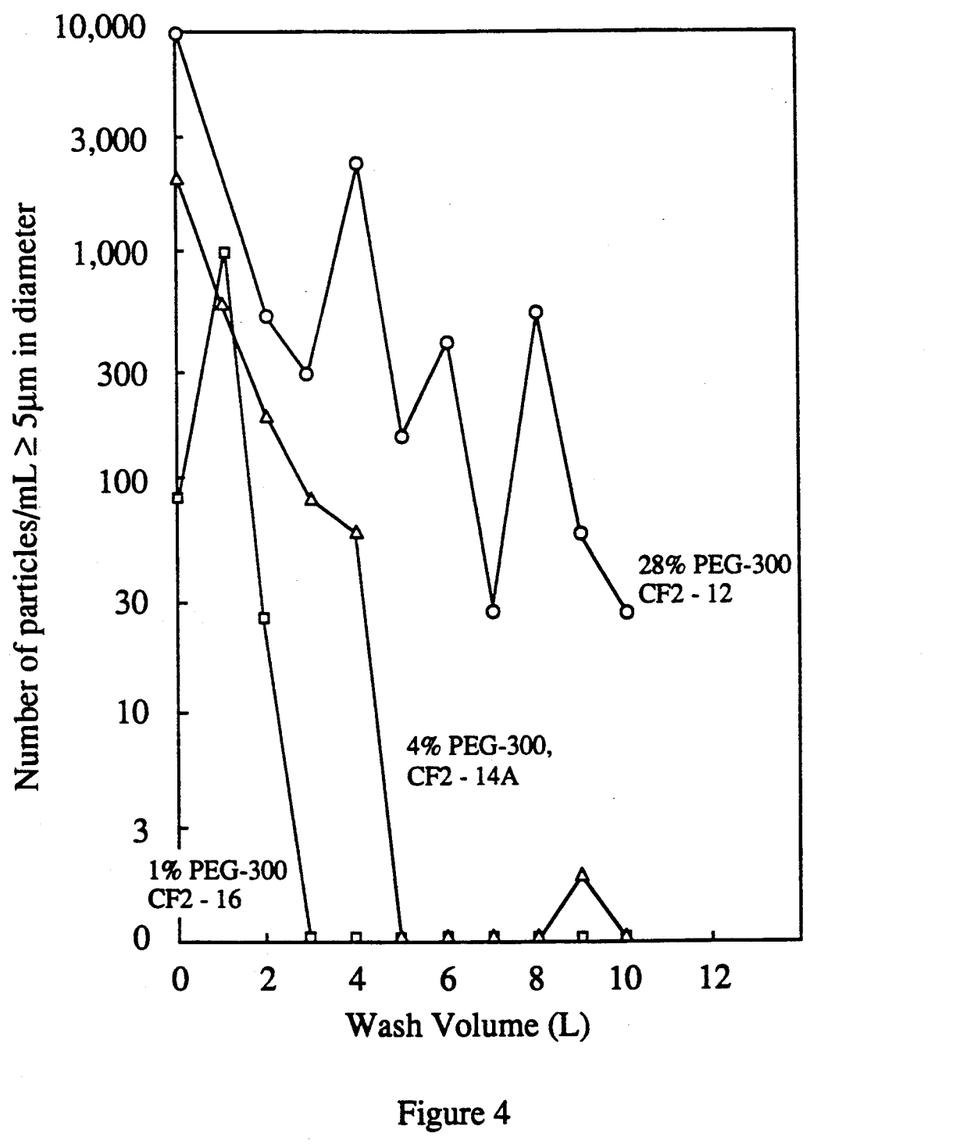

FIG. 4 shows the results for underivatized polystyrene-coated diatomite prepared as in Example 1, but with differing amounts of the pore-controlling component, PEG-300. The results indicate that the conditions of Example 1—i.e., 1% PEG-300 (the percentage being based on total polymer coat applied)—give superior results to higher amounts of the pore-controlling PEG-300 shown in FIG. 4 (4% and 28%).

Figure 5A:
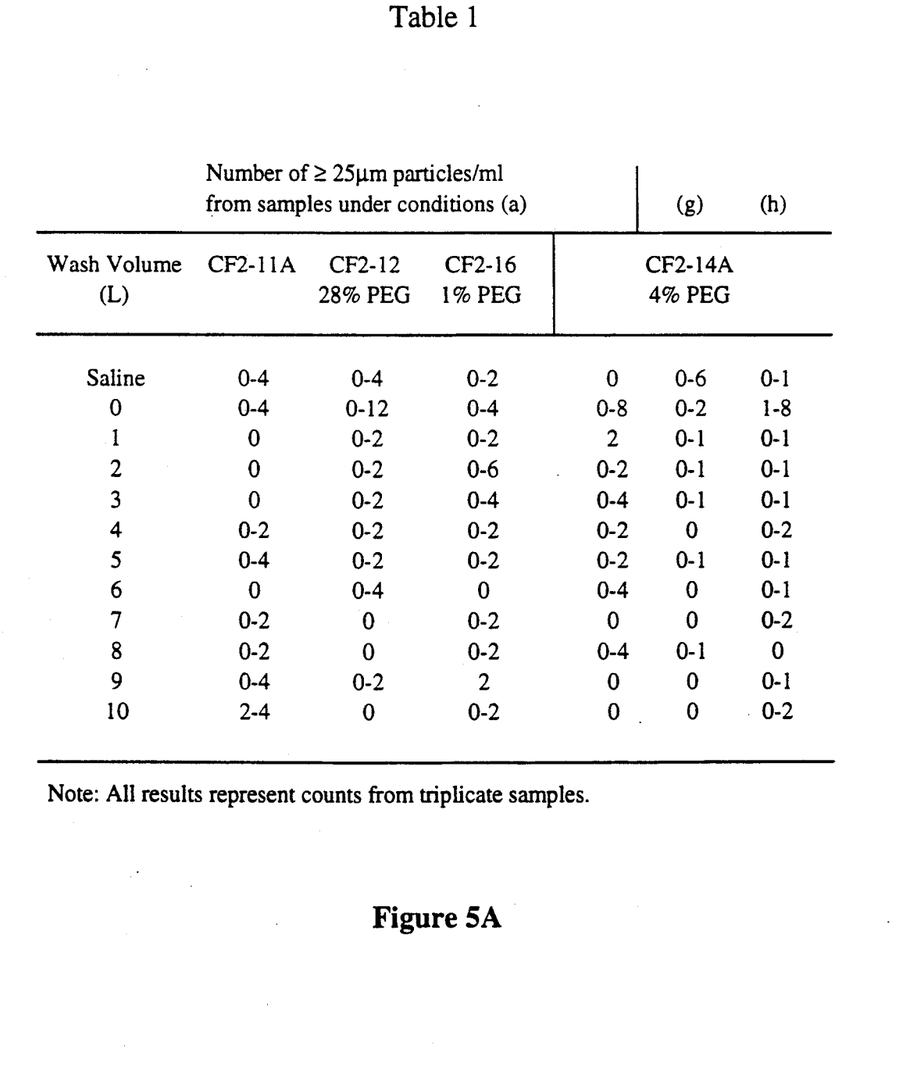
FIGS. 5A and 5B show the effect of conditions on fines shed from polystyrene coated supports.

FIG. 5A shows the results for three test compositions of FIG. 4 and the polystyrene coated positive control of FIG. 3 with regard to particles having diameters more than 25 μm. All percentages of pore-controlling component appeared to give similar counts of particles in this size range.

The procedure described above was further modified as set forth below to simulate additional conditions which might be encountered in extracorporeal treatment of fluid:

(a) Standard operating procedure with 75 g matrix contained in a cartridge, rotated dry for 1 hr in a hematology mixer, and washed with 10 l saline at 40 ml/min. Samples collected at the beginning and after each liter wash.

(b) Samples collected after temporary interruption of flow for 15 min subsequent to the above procedure (a).

(c) Samples collected after prolonged interruption of flow overnight, subsequent to the procedure (b).

(d) Samples collected after additional physical disturbance of the cartridge caused by simulated transportation, subsequent to the above procedure (c).

(e) Samples collected after increased physical disturbance introduced by rotation for 1 hr under wet conditions, subsequent to procedure (d).

(f) Samples collected after subjecting the cartridge containing the matrix to an extreme condition of physical disturbance by sudden impacts under simulated conditions, subsequent to procedure (e).

(g) Samples collected after storage of the matrix at −20° C. for 72 hr, subsequent to the standard procedure with CF2-14A followed by air drying.

(h) Samples collected after incubating the cartridge overnight at 37° C., subsequent to (g) without any other treatment.

Figure 5B:
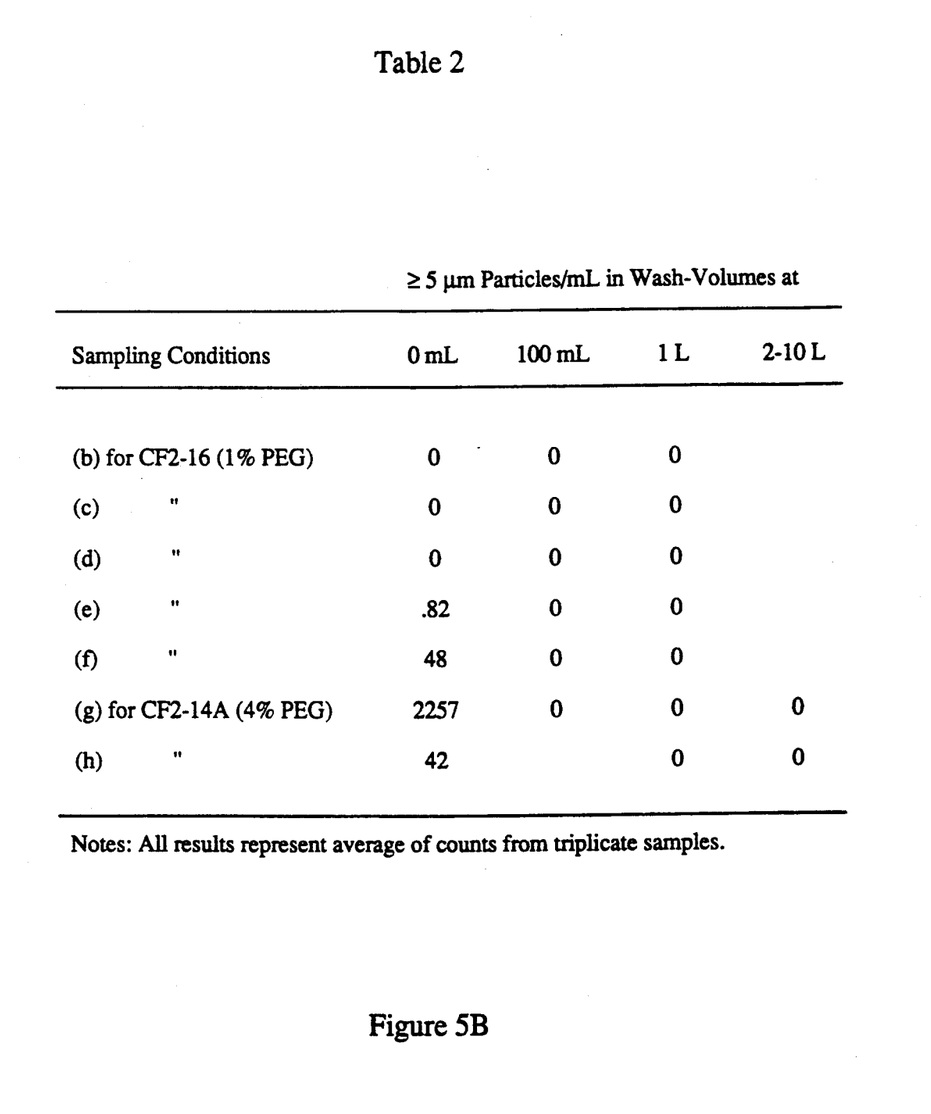

FIGS. 5A and 5B show the results, under certain of these specified conditions, and as shown in both figures, for two matrices: CF2-14A, which is 30–60 mesh diatomite with a 0.5% polystyrene coat modified with a 4% PEG-300 pore-controlling component, and CF2-16, which is the same as CF2-14A, except that only 1% PEG-300 was used. The additional treatments did not appear to affect markedly the particle count for the larger particles (FIG. 5A), but the smaller particle count could be, at least initially, dramatically affected (FIG. 5B). This happens particularly if the matrix is kept under wet conditions for a prolonged period of time (15 days or so), as was the case with sample CF2-14A tested under condition (g).

EXAMPLE 5

Assay for Biocompatibility: Hemolysis and Adsorption of Essential Blood Components Platelets are thought to be particularly adherent when polymeric substrates are contacted with blood. The extent of platelet adhesion to polystyrene-coated diatomite and similar matrices haptenized with the A trisaccharide has been determined. A 0.5 g portion of matrix was incubated with 3.75 ml of blood or saline at 37° C. by end-over-end rotation for 30 min, and the supernatants were counted for platelets (PLT), white blood cells (WBC), red blood cells (RBC) and hemoglobin (HGB). Saline was used to determine background ($\leq 1 \times 10^9/l$); fresh blood was used as control.

Test conditions assume that 100 g of matrix would be used over 4 hr for extracorporeal treatment of 6 l of whole blood from an average adult; end-over-end rotation approximates physical disturbance of flow through the cartridge. The results are shown in Table 3.

TABLE 3

Effect of Polystyrene-Coated Matrices on Various Components of Human Blood

| Matrix or Sample Used | PTL × $10^9/l$ | WBC × $10^9/l$ | RBC × $10^{12}/l$ | HGB, g/dl |
|---|---|---|---|---|
| 1) Fresh Blood | 350 | 5.1 | 4.09 | 12.8 |
| 2) Polystyrene-coated diatomite 30/60, CF2-14B | 376 | 5.9 | 3.95 | 12.9 |
| 3) Polystyrene-coated diatomite 30/60, haptenized with A-trisaccharide (CF2-20A) | 353 | 4.8 | 3.3 | 10.5 |
| 4) (3) Above pre-incubated with 1% HSA | 391 | 5.3 | 3.95 | 12.9 |

A control (4) used polystyrene-coated matrix haptenized with A trisaccharide preincubated with 1% HSA in saline to obtain a secondary coating. HSA has been shown to reduce platelet adhesion to polymer surfaces (Neumann et al, supra). These results show there is little if any nonspecific adsorption of essential blood components to the matrix.

The matrices were also tested to determine whether appreciable hemolysis occurred when blood is placed in contact with them. Details of the hemolysis assay are as follows:

One or two grams of matrix were placed separately in test tubes containing 5 or 10 mL of 0.9% saline. A 0.1 mL sample of human blood previously collected was added directly to each tube containing 1 gm matrix and saline or to 5 mL of saline extracted from the mixture of 2 g matrix incubated at 70° C. for 24 hr. Similarly, 0.1 mL blood was added to a tube of saline which acted as the negative control (no hemolysis) and also to a tube of distilled water which acted as the positive control (100% hemolysis). The contents of all the tubes were gently mixed and incubated in a water bath at 37° C. for one hr. After removing the samples of matrix (direct contact method), the blood-saline mixtures were centrifuged at 2,200 rpm for 5 min, and the absorbance of each supernatant solution was determined spectrophotometrically at 545 nm. Percentage hemolysis was determined as the difference between the absorbances of the test and negative controls divided by the absorbance of the positive control, times 100. By the extraction method the results were in the range of 0.13–0.32%; by the direct method 0.53–0.73% hemolysis were noted for CF2-14B and CF2-20A. (Less than 5% is considered non-hemolytic).

EXAMPLE 6

Efficacy of Coated Matrix in Specific Adsorption

An in vitro hemagglutination assay was used to show efficacy of the coated matrix in adsorbing an illustrative ligand antibody to ATS. 25 mg of matrix, haptenized to A trisaccharide, is incubated with 0.5 ml O-plasma serum (which contains anti-$A_1$) with rotation on a hematology mixer for 1 hr at room temperature (21° C.). The supernatant is removed and tested for hemagglutination by IgM and IgG in serial dilutions with A antigen-bearing red blood cells.

The results are shown in Table 4.

TABLE 4

Adsorption of anti-$A_1$ by Coated Matrices

| Material Tested | Solvent/ Nonsolvent in Coating Solution | Human anti-$A_1$ Titers | | | |
|---|---|---|---|---|---|
| | | IgM | IgG | IgM | IgG |
| O-plasma BK7-17 | | 1:128 | 1:512 | 1:128 | 1:512 |
| 0.5% Polystyrene-coated diatomite (30/60) BK7-20 (negative control) | TCE/PEG-300 | 64 | 256 | 128 | 256 |
| Haptenized diatomite (30/60) (0.7 μmole ATS/g) AM8-40IA (positive control) | (not coated) | 16 | 32 | 16 | 64 |
| 0.5% Polystyrene-coated haptenized diatomite (30/60) CF2-19A | TCE/PEG-300 | 8 | 32 | 16 | 32 |
| 0.5% Polyether urethane-coated haptenized diatomite (30/60) CF2-22A1 | DMF/none | 32 | 128 | 32 | 128 |
| 0.36% Collodion-coated haptenized diatomite (30/60) CF2-19B | EtOH/none | 32 | 64 | 32 | 64 |
| Precoated diatomite coupled with ATS-BSA after glutaraldehyde activation (0.43 μmole ATS/g) BK7-20A | TCE/PEG-300 | 16 | 64 | 16 | 64 |
| Precoated diatomite coupled with ATS-BSA in presence of glutaraldehyde (0.09 μmole ATS/g) BK7-20A1 | TCE/PEG-300 | 8 | 32 | 8 | 32 |
| 1% PDMS-coated haptenized diatomite (30/60) CF2-27A | DCM/none | | | 8 | 16 |
| 1% PVA-coated haptenized diatomite (30/60) CF2-29 | H2O/cross-linking reagents | | | 8 | 16 |
| Haptenized diatomite (100/120 mesh) (0.59 μmole ATS/g) AS7-30 (positive control) | (not coated) | | | 2 | 4 |
| 1% cellulose acetate-coated diatomite CF1-46B | Acetone/H2O | | | 2 | 2 |
| 1% Nylon-66 coated diatomite CF1-47C2 | HCOOH/none | | | 4 | 2 |
| 1% PSMA-coated diatomite CF1-47B2 | DMF/none | | | 8 | 16 |
| 1% Polystyrene-coated diatomite CF1-58A1 | DMF/none | | | 2 | 4 |
| 1% Polysulfone-coated diatomite CF1-58B1 | DMF/none | | | 2 | 4 |
| 1% Polystyrene-coated diatomite CF1-58C2 | TCE/PVP | | | 2 | 4 |
| 1% Polysulfone-coated diatomite CF1-58D2 | DMF/PVP | | | 2 | 4 |
| 0.2% BSA-coated diatomite CF1-73A2 | Phosphate buffer/ cross-linking reagent | | | 4 | 2 |
| 0.5% BSA-coated diatomite CF1-73B2 | Phosphate buffer/ cross-linking reagent | | | 8 | 4 |
| 1.0% BSA-coated diatomite CF1-73C2 | Phosphate buffer/ cross-linking reagent | | | 32 | 16 |

Polystyrene-coated immunoadsorbent A is clearly as effective as its uncoated haptenized form. Immunosorbents with reduced particle size (100/120 mesh) also show increased effectiveness; the results also indicate that the method of conjugation of antigen (ATS-BSA) affects efficacy.

EXAMPLE 7

Performance in Simulated Hemoperfusion

To simulate extracorporeal perfusion procedures pooled porcine blood (6 l) obtained from a local slaughterhouse was anticoagulated further with a solution of heparin and sodium citrate in normal saline and continuously recirculated through a cartridge containing 150 g of the polystyrene coated A trisaccharide-derivatized diatomite, prepared in Example 1, at 40 ml/min at room temperature (21° C.) for 4.5 hours. Samples were collected at half-hour intervals, and analyzed for total protein, albumin, bilirubin, cholesterol, alkaline phosphatase and lactate dehydrogenase. Very little or no changes in concentration of these components was found.

Antibody titers in the perfused blood were determined using human $A_1$RBC as described in Example 6. Initial titers for anti-$A_1$ (IgM/IgG) in porcine plasma were 64/128; these values dropped to 16/32 after 2 hours of hemoperfusion.

I claim:

1. An affinity matrix suitable for extracorporeal perfusion of a body fluid for the selective removal of specific components or for chromatography which comprises:

(a) a solid, particulate support derivatized to a specific affinity ligand, wherein said derivatized support is (b) coated with a biocompatible polymer, wherein the polymer coating is an integral membrane-type coating, and wherein the membrane coating has a pore size of at least 20 angstroms, and wherein said coating prevents the leaching of fine particles from the matrix.

2. The matrix of claim 1 wherein the support is an inert inorganic particulate.

3. The matrix of claim 2 wherein the support is selected from synthetic, mineral or biogenic silicates.

4. The matrix of claim 3 wherein the support is diatomite.

5. The matrix of claim 1 wherein the affinity ligand is a carbohydrate moiety.

6. The matrix of claim 5 wherein the carbohydrate moiety is selected from the oligosaccharide of FIG. 2.

7. The matrix of claim 6 wherein the carbohydrate moiety is A trisaccharide (ATS).

8. The matrix of claim 7 wherein the affinity ligand is conjugated to the support through a linker arm.

9. The matrix of claim 7 wherein the affinity ligand is conjugated to the support through a carrier.

10. The matrix of claim 9 wherein the carrier is BSA.

11. The matrix of claim 1 wherein the polymer coating is selected from polystyrene, polysulfone, polyether urethane, polydimethylsiloxane, PSMA and BSA.

12. The matrix of claim 6 wherein the carbohydrate moiety is B trisaccharide (BTS).

13. A coated support prepared by a method to coat a particulate support with a biocompatible membrane-type coating of pore size of at least 20 angstroms, wherein the coating prevents the leaching of fine particles from a matrix formed by the method, which method comprises:
   preparing a suspension of the particulate support, wherein said support is functionalized or derivatized with an affinity ligand,
   in a solvent containing dissolved biocompatible polymer in an amount 0.1-1% of the weight of the support; and
   removing the solvent from the suspension, under conditions which result in a thin, integral membrane.

14. A coated support prepared by a method to coat a particulate support with a biocompatible membrane-type coating of pore size at least 20 angstroms, wherein the coating prevents the leaching of fine particles from a matrix formed by the method, which method comprises:
   preparing a suspension of the particulate support, wherein said support is functionalized or derivatized with an affinity ligand,
   in a solvent containing dissolved biocompatible polymer in an amount 0.1-1% of the weight of the support, said solvent further containing a dissolved compatible pore-controlling component in an amount 0.5-5% of the weight of said polymer;
   removing the solvent from the suspension; and
   removing the pore-controlling component from the coating, under conditions which results in a thin, integral membrane.

* * * * *